US007135464B2

(12) United States Patent
Joshi-Hangal et al.

(10) Patent No.: US 7,135,464 B2
(45) Date of Patent: Nov. 14, 2006

(54) METHOD OF ADMINISTERING DECITABINE

(75) Inventors: Rajashree Joshi-Hangal, Union City, CA (US); Xichen Zhang, Thousand Oaks, CA (US); Stephanie Gong, Pleasanton, CA (US); Sanjeev Redkar, Union City, CA (US); Ashok Y. Gore, San Ramon, CA (US)

(73) Assignee: SuperGen, Inc., Dublin, CA (US)

( * ) Notice: Subject to any disclaimer, the term of this patent is extended or adjusted under 35 U.S.C. 154(b) by 13 days.

(21) Appl. No.: 10/890,755

(22) Filed: Jul. 13, 2004

(65) Prior Publication Data

US 2004/0259821 A1    Dec. 23, 2004

Related U.S. Application Data

(62) Division of application No. 10/164,276, filed on Jun. 5, 2002, now Pat. No. 6,982,253.

(51) Int. Cl.
*A01N 43/04* (2006.01)
*A61K 31/70* (2006.01)
*A61K 9/00* (2006.01)

(52) U.S. Cl. .............................. 514/49; 514/42; 514/43
(58) Field of Classification Search ................. 514/42, 514/43, 49
See application file for complete search history.

(56) References Cited

U.S. PATENT DOCUMENTS

| | | | |
|---|---|---|---|
| 3,817,980 A | 6/1974 | Vorbruggen et al. | |
| 4,022,889 A | 5/1977 | Bannister et al. | |
| 4,477,442 A | 10/1984 | Skulnick et al. | |
| 4,684,630 A * | 8/1987 | Repta et al. | 514/49 |
| 4,690,918 A | 9/1987 | Beppu et al. | |
| 4,910,021 A | 3/1990 | Davis et al. | |
| 5,654,286 A | 8/1997 | Hostetler | |
| 5,700,640 A | 12/1997 | Voss et al. | |
| 5,736,531 A | 4/1998 | Von Borstel et al. | |
| 5,856,090 A | 1/1999 | Epstein | |
| 5,856,094 A | 1/1999 | Sidransky et al. | |
| 5,968,914 A | 10/1999 | Von Borstel et al. | |
| 6,136,791 A | 10/2000 | Nyce | |
| 6,225,325 B1 | 5/2001 | Jacob | |
| 6,255,293 B1 | 7/2001 | Kimchi | |
| 6,309,666 B1 | 10/2001 | Hatano et al. | |
| 6,613,753 B1 | 9/2003 | Rubinfeld et al. | |
| 6,905,669 B1 * | 6/2005 | DiMartino | 424/9.1 |
| 2001/0012835 A1 | 8/2001 | Fine et al. | |
| 2002/0114809 A1 | 8/2002 | Rubinfeld et al. | |
| 2002/0136709 A1 | 9/2002 | Zahner | |
| 2003/0013099 A1 | 1/2003 | Lasek et al. | |
| 2003/0039689 A1 | 2/2003 | Chen et al. | |
| 2003/0045497 A1 | 3/2003 | Widegren et al. | |
| 2003/0108588 A1 | 6/2003 | Chen et al. | |
| 2003/0147813 A1 | 8/2003 | Lyons | |
| 2003/0165864 A1 | 9/2003 | Lasek et al. | |
| 2003/0171303 A1 | 9/2003 | Gallop et al. | |
| 2003/0229047 A1 | 12/2003 | Joshi-Hangal et al. | |

FOREIGN PATENT DOCUMENTS

| | | |
|---|---|---|
| CS | 269077 | 12/1963 |
| DE | 1922702 | 5/1969 |
| DE | 2105468 | 2/1971 |
| EP | 286958 | 4/1988 |
| JP | 05219974 | 2/1992 |
| JP | 2002223753 | 1/2001 |
| JP | 2002370939 | 6/2001 |
| JP | 2003310293 | 4/2002 |
| WO | WO 93/01202 | 7/1991 |
| WO | WO 94/26761 | 5/1993 |
| WO | WO 94/27632 | 6/1993 |
| WO | WO 96/11280 | 10/1994 |
| WO | WO 96/36693 | 5/1995 |
| WO | WO 96/39035 | 6/1995 |
| WO | WO 96/40165 | 6/1995 |
| WO | WO 98/14619 | 10/1996 |
| WO | WO 98/16186 | 10/1996 |
| WO | WO 98/29108 | 12/1996 |
| WO | WO 98/54318 | 5/1997 |
| WO | WO 00/05419 | 7/1998 |
| WO | WO 00/23112 | 10/1998 |
| WO | WO 00/40269 | 1/1999 |
| WO | WO 00/54574 | 3/1999 |
| WO | WO 00/62075 | 4/1999 |
| WO | WO 01/21215 A1 | 9/1999 |

(Continued)

OTHER PUBLICATIONS

Lin et al. Journal of Pharmaceutical Sciences (1981), vol. 70 (11), pp. 1228-1232.*
Von Hoff, et al., "5-Azacytidine. A New Anticancer Drug With Effectiveness in Acute Myelogenous Leukemia," *Annals of Internal Medicine* (1976) 85(2), pp. 237-245.
Sheikhnejad, G. et al., "Mechanism of inhibition of DNA (cytosine C5)-methyltransferases by oligodeoxyribonucleotides containing 5,6-dihydro-5-azacytosine", *J. Mol. Biol.*, 1999, pp. 2021-2034, vol. 285.

(Continued)

*Primary Examiner*—Patrick T. Lewis
(74) *Attorney, Agent, or Firm*—Wilson Sonsini Goorich & Rosati

(57) ABSTRACT

Pharmaceutical formulations, kits and vessels are provided for delivering decitabine to a patient suffering from a disease in need of treatment with decitabine. The pharmaceutical formulation comprises decitabine solvated in a non-aqueous solvent that comprises glycerin, propylene glycol, polyethylene glycol, or combinations. Such formulations are more chemically stable than conventional liquid formulations of decitabine containing more than 40% water in volume. The pharmaceutical formulations can be used for any disease that is sensitive to the treatment with decitabine, such as hematological disorders and cancer.

11 Claims, No Drawings

FOREIGN PATENT DOCUMENTS

| | | |
|---|---|---|
| WO | WO 01/69262 A1 | 3/2000 |
| WO | WO 01/79164 A2 | 3/2000 |
| WO | WO 02/18592 A1 | 9/2000 |
| WO | WO 02/21140 A1 | 9/2000 |
| WO | WO 02/051980 A2 | 12/2000 |
| WO | WO 02/057425 A2 | 1/2001 |
| WO | WO 02/076486 A2 | 2/2001 |
| WO | WO 02/083705 A1 | 4/2001 |
| WO | WO 02/085400 A1 | 4/2001 |
| WO | WO 02/087586 A1 | 4/2001 |
| WO | WO 03/006950 A2 | 7/2001 |
| WO | WO 03/011209 A2 | 7/2001 |
| WO | WO 03/012085 A1 | 7/2001 |
| WO | WO 03/012112 A1 | 7/2001 |
| WO | WO 03/026574 A2 | 9/2001 |
| WO | WO 03/031932 A2 | 10/2001 |
| WO | WO 03/040363 A1 | 11/2001 |
| WO | WO 03/043631 A2 | 11/2001 |
| WO | WO 03/045427 A2 | 11/2001 |
| WO | WO 03/046190 A1 | 11/2001 |
| WO | WO 03/065995 A2 | 2/2002 |
| WO | WO 03/076593 A2 | 3/2002 |
| WO | WO 03/076594 A2 | 3/2002 |
| WO | WO 03/086374 A1 | 4/2002 |
| WO | WO 2003/087774 A3 | 4/2002 |
| WO | WO 03/104427 A2 | 6/2002 |
| WO | WO 2004/009023 A2 | 7/2002 |
| WO | WO 02/069903 | 9/2002 |
| WO | PCT/US04/22367 | 7/2005 |

OTHER PUBLICATIONS

Goffin, J. et al., "DNA methyltransferase inhibitors—state of the art", *Annals of Oncology*, 2002, pp. 1699-1716, vol. 13.

Wijermans, P. et al., "Low-dose 5-aza-2'-deoxycytidine, a DNA hypomethylating agent, for the treatment of high-risk myelodysplastic syndrome: a multicenter phase II study in elderly patients", *Journal of Clinical Oncology*, Mar. 2000, pp. 956-962, vol. 18, No. 5.

Brown, R. et al. Demethylation of DNA by decitabine in cancer chemotherapy. *Expert Rev Anticancer Ther.* 2004; 4(4): 501-510.

Gilbert, J. et al. The Clinical Application of Targeting Cancer through Histone Acetylation and Hypomethylation. *Clinical Cancer Research.* 2004; 10: 4589-4596.

Herman, J. G. et al. Gene Silencing in Cancer in Association with Promoter Hypermethylation. *The New England Journal of Medicine.* 2003; 349(21): 2042-2054.

Leone, G. et al. DNA methylation and demethylating drugs in myelodysplastic syndromes and secondary leukemias. *Haematologica.* 2002; 87(12): 1324-1341.

Leone, G. et al. Inhibitors of DNA methylation in the treatment of hematological malignancies and MDS. *Clin Immunol.* 2003; 109(1): 89-102.

\* cited by examiner

METHOD OF ADMINISTERING DECITABINE

This application is a Division of U.S. Ser. No. 10/164,276, filed Jun. 5, 2002 now U.S. Pat. No. 6,982,253, which is incorporated herein by reference in its entirety.

BACKGROUND OF THE INVENTION

1. Field of the Invention

The present invention relates to methods and compositions for preparing, formulating and administering decitabine to a host in need thereof.

2. Description of Related Art

Decitabine, 5-aza-2'-deoxycytidine, is an antagonist of its related natural nucleoside, deoxycytidine. The only structural difference between these two compounds is the presence of a nitrogen at position 5 of the cytosine ring in decitabine as compared to a carbon at this position for deoxycytidine. Two isomeric forms of decitabine can be distinguished. The β-anomer is the active form. The modes of decomposition of decitabine in aqueous solution are (a) conversion of the active b-anomer to the inactive α-anomer (Pompon et al. (1987) J. Chromat. 388:113–122); (b) ring cleavage of the aza-pyrimidine ring to form N-(formylamidino)-N'-β-D-2'-deoxy-(ribofuranosy)-urea (Mojaverian and Repta (1984) J. Pharm. Pharmacol. 36:728–733); and (c) subsequent forming of guanidine compounds (Kissinger and Stemm (1986) J. Chromat. 353:309–318).

Decitabine possesses multiple pharmacological characteristics. At a molecular level, it is S-phase dependent for incorporation into DNA. At a cellular level, decitabine can induce cell differentiation and exert hematological toxicity. Despite having a short half life in vivo, decitabine has an excellent tissue distribution.

The most prominent function of decitabine is its ability to specifically and potently inhibit DNA methylation. Methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine. Momparler et al. (1985) 30:287–299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109–114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797–11801. By specifically inhibiting DNA methyltransferase, the enzyme required for methylation, the aberrant methylation of the tumor suppressor genes can be prevented.

Decitabine is commonly supplied as a sterile lyophilized powder for injection, together with buffering salt, such as potassium dihydrogen phosphate, and pH modifier, such as sodium hydroxide. For example, decitabine is supplied by SuperGen, Inc., as lyophilized powder packed in 20 mL glass vials, containing 50 mg of decitabine, monobasic potassium dihydrogen phosphate, and sodium hydroxide. When reconstituted with 10 mL of sterile water for injection, each mL contain 5 mg of decitabine, 6.8 mg of $KH_2PO_4$, and approximately 1.1 mg NaOH. The pH of the resulting solution is 6.5–7.5. The reconstituted solution can be further diluted to a concentration of 1.0 or 0.1 mg/mL in cold infusion fluids, i.e., 0.9% Sodium Chloride; or 5%. Dextrose; or 5% Glucose; or Lactated Ringer's. The unopened vials are typically stored under refrigeration (2–8° C.; 36–46° F.), in the original package.

Decitabine is most typically administrated to patients by injection, such as by a bolus I.V. injection, continuous I.V. infusion, or I.V. infusion. The length of I.V. infusion is limited by decitabine's decomposition in aqueous solutions.

A need still exists for improved methods and compositions for preparing decitabine, formulating decitabine and for administering decitabine. The present invention provides such improvements.

SUMMARY OF THE INVENTION

The present invention provides innovative liquid formulations of decitabine. According to the invention, decitabine is solvated in non-aqueous solvent such as glycerin, propylene glycol, polyethylene glycol, or combinations thereof. The inventive approach circumvents problems associated with aqueous formulations of decitabine containing at least 40% water, such as chemical instability, inconvenient storage and transportation, and discomfort of patients due to cold infusions. The formulations can be used to treat a wide variety of indications that are sensitive to decitabine treatment.

In one aspect of the invention, a liquid pharmaceutical formulation is provided for administering decitabine to a patient. In one embodiment, the formulation comprises decitabine solvated in a solvent that comprises glycerin, propylene glycol, polyethylene glycol, or combinations thereof.

According to the embodiment, the amount of decitabine in the pharmaceutical formulation is between 0.1 and 200 mg per ml of solvent, optionally between 1 and 100, between 2 mg and 50 mg, 5 mg and 30 mg, between 10 mg and 25 mg per ml of the solvent.

Optionally, the pharmaceutical formulation may comprise 40%, 20%, 10%, 5%, 2% or less water. In one variation, the pharmaceutical formulation is anhydrous and may optionally further comprise a drying agent.

The pharmaceutical formulation may also optionally comprise one or more drying agents, antioxidants and/or antimicrobials.

According to the embodiment, examples of polyethylene glycol (PEG) include, but are not limited to, PEG300, PEG400 and PEG1000.

According to the embodiment, the solvent is a combination of propylene glycol and glycerin, wherein the concentration of propylene glycol in the solvent is between 0.1–99.9%, optionally between 1–90%, between 10–60%, or between 20–40%.

Also according to the embodiment, the solvent is a combination of polyethylene glycol and glycerin, wherein the concentration of polyethylene glycol in the solvent is between 0.1–99.9%, optionally between 1–90%, between 10–60%, or between 20–40%.

Also according to the embodiment, the solvent is a combination of propylene glycol, polyethylene glycol and glycerin, wherein the concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–60%, or between 20–40%.

Also according to the embodiment, the pharmaceutical formulation may further comprise an acidifying agent added to the formulation in a proportion such that the formulation has a resulting pH between about 4 and 8. Adding an acidifying agent to the formulation is believed to facilitate ready dissolution of decitabine in the solvent and enhance long-term stability of the formulation.

The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

In a variation, the acidifying agent is ascorbic acid at a concentration of 0.01–0.2 mg/ml of the solvent, optionally 0.04–0.1 mg/ml or 0.03–0.07 mg/ml of the solvent.

The pH of the pharmaceutical formulation may be adjusted to be between pH 4 and pH 8, preferably between pH 5 and pH 7, and more preferably between pH 5.5 and pH 6.8.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrox, cyclodextrin such as, α-, β-, and γ-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted α-, β-, and γ-cyclodextrin.

The pharmaceutical formulation is preferably at least 80%, 90%, 95% or more stable upon storage at 25° C. for 7, 14, 21, 28 or more days. The pharmaceutical formulation is also preferably at least 80%, 90%, 95% or more stable upon storage at 40° C. for 7, 14, 21, 28 or more days.

In another embodiment, the pharmaceutical formulation is prepared by the act comprising:

dissolving decitabine in a non-aqueous solvent that comprises glycerin, propylene glycol, polyethylene glycol, or a combination thereof.

According to the embodiment, the act further comprise: micronizing decitabine. Micronization of decitabine is believed to accelerate the rate of dissolution of decitabine in the solvent. Decitabine may be micronized until the size of at least 90% of the particles is below 20 microns, and optionally, the size of at least 50% of the particles is below 10 microns.

According to the embodiment, the act further comprise: adding an acidifying agent to the solution containing decitabine and the solvent such that pH of the resulting solution is between pH 4 and pH 8, preferably between pH 5 and pH 7, and more preferably between pH 5.5 and pH 6.8.

In yet another embodiment, the pharmaceutical formulation is prepared by the acts of:

(a) adding an acidifying agent to propylene glycol;
(b) adding glycerin to the acidified propylene glycol prepared by act (a); and
(c) adding solid decitabine to the acidified mixture of propylene glycol and glycerin prepared by act (b).

According to the embodiment, the acidifying agent may be ascorbic acid, preferably crystalline powder of ascorbic acid. The solid decitabine may be micronized decitabine. The size of at least 90% of the micronized decitabine particles is below 20 microns, and optionally, the size of at least 50% of the particles is below 10 microns.

According to the embodiment, the acts may further comprise:

(d) agitating the mixture prepared by act (c).

The act of agitating may include sonication or any mode of agitation that results in a clear solution of the pharmaceutical formulation.

The pharmaceutical formulation may also optionally comprise one or more therapeutic agents other than decitabine. For example, the pharmaceutical formulation may optionally further comprise a therapeutic agent selected from the group consisting of anti-neoplastic agents, alkylating agents, agents that are members of the retinoids superfamily, hormonal agents, plant-derived agents, biologic agents, interleukins, interferons, cytokines, immuno-modulating agents, and monoclonal antibodies.

In another aspect of the invention, a sterilized vessel is provided for administering decitabine to a host in need thereof. In one embodiment, the sterilized vessel comprises a pharmaceutical formulation according to the present invention. The vessel, for example, may be a vial, syringe, or ampoule. The vessel may come in different sizes. For example, the vessel may comprise between 1 and 50, 1 and 25, 1 and 20 or 1 and 10 ml of the pharmaceutical formulation.

In yet another aspect of the invention, a kit is provided for administering decitabine to a host in need thereof. In one embodiment, the kit comprises decitabine in a solid, preferably powder form, and a non-aqueous diluent that comprises glyercin, propylene glycol, polyethylene glycol, or combinations thereof. Mixing of the solid decitabine and the diluent results in the formation of a pharmaceutical formulation according to the present invention. For example, the kit may comprise a first vessel comprising decitabine in a solid form; and a vessel container comprising a diluent that comprises glyercin; wherein adding the diluent to the solid decitabine results in the formation of a pharmaceutical formulation for administering decitabine. Mixing the solid decitabine and diluent may optionally form a pharmaceutical formulation that comprises between 0.1 and 200 mg decitabine per ml of the diluent, optionally between 1 and 100, between 2 mg and 50 mg, 5 mg and 30 mg, between 10 mg and 25 mg per ml of the solvent.

According to the embodiment, the diluent is a combination of propylene glycol and glycerin, wherein the concentration of propylene glycol in the solvent is between 0.1–99.9%, optionally between 1–90%, between 10–80%, or between 50–70%.

Also according to the embodiment, the diluent is a combination of polyethylene glycol and glycerin, wherein the concentration of polyethylene glycol in the solvent is between 0.1–99.9%, optionally between 1–90%, between 10–80%, or between 50–70%.

Also according to the embodiment, the diluent is a combination of propylene glycol, polyethylene glycol and glycerin, wherein the concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–60%, or between 20–40%.

The diluent also optionally comprises 40%, 20%, 10%, 0.5%, 2% or less water. In one variation, the diluent is anhydrous and may optionally further comprise a drying agent. The diluent may also optionally comprise one or more drying agents, glycols, antioxidants and/or antimicrobials.

The kit may optionally further include instructions. The instructions may describe how the solid decitabine and the diluent should be mixed to form a pharmaceutical formulation. The instructions may also describe how to administer the resulting pharmaceutical formulation to a patient. It is noted that the instructions may optionally describe the administration methods according to the present invention.

The diluent and decitabine may be contained in separate vessels. The vessels may come in different sizes. For example, the vessel may comprise between 1 and 50, 1 and 25, 1 and 20, or 1 and 10 ml of the diluent.

In yet another aspect of the invention, a method is provided for administering decitabine to a host in need of, such as a patient suffering from a disease that is sensitive to the treatment with decitabine. The decitabine-containing pharmaceutical formulation of the present invention may be administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. Preferably, the pharmaceutical formulation is administered intravenously, intramuscularly, or subcutaneously.

In one embodiment, the method comprises: administering to the patient a therapeutically effective amount of decitabine in a pharmaceutical formulation according to the present invention. Optionally, the pharmaceutical formulation comprises 40%, 20%, 10%, 5%, 2% or less water prior to administration to the patient. The pharmaceutical formulation may also be anhydrous prior to administration to the patient.

The method may further comprise administering a therapeutic agent other than decitabine in combination with the pharmaceutical formulation. For example, the pharmaceutical formulation may further comprise a therapeutic agent selected from the group consisting of anti-neoplastic agents, alkylating agents, agents that are members of the retinoids superfamily, hormonal agents, plant-derived agents, biologic agents, interleukins, interferons, cytokines, immunomodulating agents, and monoclonal antibodies.

In another embodiment, the method comprises: taking a pharmaceutical formulation comprising between 0.1 and 200 mg decitabine solvated in a non-aqueous solvent that comprises glycerin, propylene glycol, polyethylene glycol, or combinations thereof; diluting the pharmaceutical formulation with an aqueous solution; and administering the resulting diluted pharmaceutical formulation; wherein the dilution is performed 10 hr, 2 hr, 1 hr, 30 min, 10 min, 5 min or less before administration.

In yet another embodiment, the method comprises: taking a pharmaceutical formulation comprising between 0.1 and 200 mg decitabine solvated in a non-aqueous solvent that comprises glycerin, propylene glycol, polyethylene glycol, or combinations thereof; admixing aliquots of the pharmaceutical formulation with an aqueous solution at ambient temperature; and infusing the resulting solution into the patient's body. A Y connector is optionally used to admix the aliquots of the pharmaceutical formulation with the aqueous solution at ambient temperature. This allows the infusion to be optionally performed over a period of 3, 4, 5 or more hours. Such a mode of administration is believed to cause less discomfort in the patient and allow slower and longer infusion time than that needed for administering decitabine formulated in conventional ways, such as decitabine reconstituted in cold WFI and further diluted with cold infusion fluid.

Related to the kit, a method is also provided that comprises mixing decitabine that is in a solid, preferably powder form with a diluent to form a pharmaceutical formulation, and administering the pharmaceutical formulation to a patient. Advantageously, the pharmaceutical formulation may be formed by mixing the decitabine with the diluent shortly prior to administration to a patient (e.g., within one day, or even 6, 5, 4, 3, 2 or 1 hours or less before administration). This reduces decomposition of the decitabine. Optionally, as described herein, the glycerin pharmaceutical formulation may be administered by admixing aliquots of the pharmaceutical formulation with an aqueous solution; and infusing the resulting solution into the patient's body, optionally with a Y connector as also described herein.

DETAILED DESCRIPTION OF THE INVENTION

The present invention is directed to pharmaceutical formulations comprising decitabine and a non-aqueous solvent for decitabine. Compared with decitabine formulation prepared by reconstituting decitabine powder in aqueous solvent, the inventive formulations offer long-term chemical stability, convenient storage and administration, and cause less discomfort to patients due to cold infusions. The pharmaceutical formulations of the present invention can be used to treat patient suffering from a disease sensitive to the treatment with decitabine, such as hematological disorders, benign tumors, malignant tumors, restenosis, and inflammatory diseases via various routes of administration such as intravenous, intramuscular, or subcutaneous injection.

1. Pharmaceutical Formulations of the Present Invention

The present invention generally relates to pharmaceutical formulations comprising decitabine solvated in non-aqueous solvent that includes glycerin, propylene glycol, polyethylene glycol, or combinations thereof. The present invention also generally relates to methods and kits for administering these pharmaceutical formulations to a host such as a patient suffering from a disease that is sensitive to the treatment of decitabine.

It is believed that it is important for decitabine to be stable in the pharmaceutical formulations so that the pharmaceutical formulations may be stored for a prolonged period of time prior to use. In current clinical treatment with decitabine, to minimize drug decomposition decitabine is supplied as lyophilized powder and reconstituted in a cold aqueous solution containing water in at least 40% vol of the solvent, such as WFI, and diluted in cold infusion fluids prior to administration. Such a formulation and treatment regimen suffers from a few drawbacks. First, refrigeration of decitabine in cold solution becomes essential, which is burdensome in handling and economically less desirable than a formulation that can sustain storage at higher temperatures. Second, due to rapid decomposition of decitabine in aqueous solution, the reconstituted decitabine solution may only be infused to a patient for a maximum of 3 hr if the solution has been stored in the refrigerator for less than 7 hr. In addition, infusion of cold fluid can cause great discomfort and pain to the patient, which induces the patient's resistance to such a regimen.

In contrast, the present invention provides pharmaceutical formulations that can circumvent the above-listed problems associated with the current clinical treatment with decitabine. The inventive formulations are directed to decitabine solvated in non-aqueous solvent such as glycerin, propylene glycol, polyethylene glycol, or combinations thereof. These formulations are believed to be more chemically stable than decitabine formulated in aqueous solutions containing water in at least 40% vol. of the solvent. In a preferred embodiment, the inventive formulation contains less than 1% water in the solvent. This formulation contains essentially non-aqueous solvent such as propylene glycol. Owing to the enhanced stability, the inventive formulation may be stored and transported at ambient temperature, thereby significantly reducing the cost of handling the drug. Further, the inventive formulation may be conveniently stored for a long time before being administered to the patient. In addition, the inventive formulation may be diluted with regular infusion fluid (without chilling) and administered to a patient at room temperature, thereby avoiding causing patients' discomfort associated with infusion of cold fluid.

In one embodiment, decitabine is dissolved in glycerin at different concentrations. For example, the formulation may optionally comprise between 0.1 and 200; between 1 and 100; between 1 and 50; between 2 and 50; between 2 and 100; between 5 and 100; between 10 and 100 or between 20 and 100 mg decitabine per ml of glycerin. Specific examples of decitabine per glycerin concentrations include but are not limited to 2, 5, 10, 20, 22, 25, 30, 40 and 50 mg/ml.

Different grades of glycerin (synonyms: 1,2,3-proparietriol; glycerol; glycol alcohol; glycerol anhydrous) may be used to prepare the formulations. Preferably, glycerin with chemical purity higher than 90% is used to prepare the formulations.

It is noted that water can accelerate decitabine decomposition within a pharmaceutical formulation. Accordingly, it is desirable for the pharmaceutical formulation to have a low water content. For example, the pharmaceutical formulations according to the present invention preferably comprise 40%, 20%, 10%, 5%, 2%, 1% or less of water. In one variation, the pharmaceutical formulation is stored in a substantially anhydrous form. Given the hygroscopic nature of glycerin, a drying agent may optionally be added to the pharmaceutical formulation to absorb water.

In another embodiment, decitabine is dissolved in propylene glycol at different concentrations. For example, the formulation may optionally comprise between 0.1 and 200; between 0.1 and 100; between 0.1 and 50; between 2 and 50; between 2 and 100; between 5 and 100; between 10 and 100 or between 20 and 100 mg decitabine per ml of propylene glycol. Specific examples of decitabine per propylene glycol concentrations include but are not limited to 2, 5, 10, 20, 22, 25, 30, 40 and 50 mg/ml.

In yet another embodiment, decitabine is dissolved in a solvent combining glycerin and propylene glycol at different concentrations. The concentration of propylene glycol in the solvent is between 0.1–99.9%, optionally between 1–90%, between 10–80%, or between 50–70%.

In yet another embodiment, decitabine is dissolved at different concentrations in a solvent combining glycerin and polyethylene glycol (PEG) such as PEG300, PEG400 and PEG1000. The concentration of polyethylene glycol in the solvent is between 0.1–99.9%, optionally between 1–90%, between 10–80%, or between 50–70%.

In yet another embodiment, decitabine is dissolved at different concentrations in a solvent combining propylene glycol, polyethylene glycol and glycerin. The concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–80%, or between 50–70%.

It is believed and experimentally proven that addition of propylene glycol can improve chemical stability, reduce viscosity of the formulations and facilitate dissolution of decitabine in the solvent.

The pharmaceutical formulation may further comprise an acidifying agent added to the formulation in a proportion such that the formulation has a resulting pH between about 4 and 8. The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

It is believed that adding an acidifying agent to the formulation to maintain a relatively neutral pH (e.g., within pH 4–8) facilitates ready dissolution of decitabine in the solvent and enhances long-term stability of the formulation. In alkaline solution, there is a rapid reversible decomposition of decitabine to N-(formylamidino)-N'-β-D-2-deoxyribofuranosylurea, which decomposes irreversibly to form 1-β-D-2'-deoxyribofuranosyl-3-guanylurea. The first stage of the hydrolytic degradation involves the formation of N-amidinium-N'-(2-deoxy-β-D-erythropentofuranosyl)urea formate (AUF). The second phase of the degradation at an elevated temperature involves formation of guanidine. In acidic solution, N-(formylamidino)-N'-β-D-2-deoxyribofuranosylurea and some unidentified compounds are formed. In strongly acidic solution (at pH<2.2) 5-azacytosine is produced. Thus, maintaining a relative neutral pH may be advantageous for the formulation.

In a variation, the acidifying agent is ascorbic acid at a concentration of 0.01–0.2 mg/ml of the solvent, optionally 0.04–0.1 mg/ml or 0.03–0.07 mg/ml of the solvent.

The pH of the pharmaceutical formulation may be adjusted to be between pH 4 and pH 8, preferably between pH 5 and pH 7, and more preferably between pH 5.5 and pH 6.8.

The pharmaceutical formulation is preferably at least 80%, 90%, 95% or more stable upon storage at 25° C. for 7, 14, 21, 28 or more days. The pharmaceutical formulation is also preferably at least 80%, 90%, 95% or more stable upon storage at 40° C. for 7, 14, 21, 28 or more days.

The pharmaceutical formulations may also optionally further include one or more antioxidants. Antioxidants may promote long-term stability of decitabine within the formulations. In one variation, the antioxidant is in a crystalline form. For example, crystalline ascorbic acid and ascorbate salts may be included in the formulations. Thus, a variation of the formulations may comprise decitabine solvated in glycerin and an antioxidant, optionally where the antioxidant is in a solid form.

The pharmaceutical formulations may also optionally further include one or more antimicrobials. For example, antibiotic agents may be added to the formulations. Examples of antibiotic agents include, but are not limited to, anthracyclines (e.g. doxorubicin, daunorubicin, epirubicin, idarubicin and anthracenedione), mitomycin C, bleomycin, dactinomycin, and plicatomycin. Antimicrobials may promote the therapeutic effect of the formulations.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrox, cyclodextrin such as, α-, β-, and γ-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted α-, β-, and γ-cyclodextrin. Cyclodextrins such as Encapsin® from Janssen Pharmaceuticals or equivalent may be used for this purpose.

Therapeutically active agents other than decitabine may also be used in combination with the formulations without departing from the present invention. These agents may optionally be added to the formulations. Preferably the therapeutically active agents synergistically enhance the effect of decitabine. Examples of therapeutic agents that may be used in conjunction with the pharmaceutical formulations of the present invention include, but are not limited to, anti-neoplastic agents, alkylating agents, agents that are members of the retinoids superfamily, hormonal agents, plant-derived agents, biologic agents, interleukins, interferons, cytokines, immuno-modulating agents, and monoclonal antibodies.

In one embodiment, an alkylating agent is used in combination with and/or added to the formulation. Examples of alkylating agents include, but are not limited to bischloroethylamines (nitrogen mustards; e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin).

In another embodiment, cisplatin, carboplatin or cyclophosphamide is used in combination with and/or added to the formulation.

In another embodiment, a member of the retinoids superfamily is used in combination with and/or added to the formulation. Retinoids are a family of structurally and functionally related molecules that are derived or related to vitamin A (all-trans-retinol). Examples of retinoid include, but are not limited to, all-trans-retinol, all-trans-retinoic acid (tretinoin), 13-cis retinoic acid (isotretinoin) and 9-cis-retinoic acid.

In yet another embodiment, a hormonal agent is used in combination with and/or added to the formulation. Examples of such a hormonal agent are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

In yet another embodiment, a plant-derived agent is used. Examples of plant-derived agents include, but are not limited to, vinca alkaloids (e.g., vincristine, vinblastine, vindesine, vinzolidine and vinorelbine), camptothecin (20(S)-camptothecin, 9-nitro-20(S)-camptothecin, and 9-amino-20 (S)-camptothecin), podophyllotoxins (e.g., etoposide (VP-16) and teniposide (VM-26)), and taxanes (e.g., paclitaxel and docetaxel).

In yet another embodiment, a biologic agent is used such as immuno-modulating proteins such as cytokines, monoclonal antibodies against tumor antigens, tumor suppressor genes, and cancer vaccines.

Examples of interleukins that may be used in conjunction with the decitabine formulations include, but are not limited to, interleukin 2 (IL-2), and interleukin 4 (IL-4), interleukin 12 (IL-12). Examples of interferons that may be used in conjunction with decitabine—glycerin formulations include, but are not limited to, interferon α, interferon β (fibroblast interferon) and interferon γ (fibroblast interferon). Examples of such cytokines include, but are not limited to erythropoietin (epoietin α), granulocyte-CSF (filgrastim), and granulocyte, macrophage-CSF (sargramostim). Immuno-modulating agents other than cytokines include, but are not limited to bacillus Calmette-Guerin, levamisole, and octreotide.

Example of monoclonal antibodies against tumor antigens that can be used in conjunction with the decitabine formulations, but are not limited to, HERCEPTIN® (Trastruzumab), RITUXAN® (Rituximab), MYLOTARG® (anti-CD33), and CAMPATH® (anti-CD52).

2. Methods for Preparing Pharmaceutical Formulations

Described herein are methods that may be used to form a particular embodiment of the inventive pharmaceutical formulations: a decitabine-glycerin formulation. It is noted that other methods for forming this formulation and other formulations described above in Section 1 may also be used.

In one embodiment, the formulation is prepared by taking glycerin and dissolving decitabine in the glycerin. This may be done, for example, by adding decitabine to the glycerin or by adding the glycerin to decitabine. By their admixture, the decitabine-glycerin formulation is formed.

Optionally, the method further comprises additional steps to increase the rate at which the decitabine is solvated by the glycerin. Examples of additional steps that may be performed include, but are nor limited to, agitation, heating, extension of solvation period, and application of micronized decitabine and the combinations thereof.

In one variation, agitation is applied. Examples of agitation include but are nor limited to, mechanical agitation, sonication, conventional mixing, conventional stirring and the combinations thereof. For example, mechanical agitation of the formulations may be performed according to manufacturer's protocols by Silverson homogenizer manufactured by Silverson Machines Inc., (East Longmeadow, Mass.).

In another variation, heat may be applied. Optionally, the formulations may be heated in a water bath. Preferably, the temperature of the heated formulations may be less than 70° C., more preferably, between 25° C. and 40° C. As an example, the formulation may be heated to 37° C.

In yet another variation, decitabine is solvated in glycerin over an extended period of time.

In yet another variation, micronized decitabine may also be employed to enhance solvation kinetics. Optionally, micronization may be performed by a milling process. As an example, micronization may be performed by milling process performed Mastersizerusing an Air Jet Mill, manufactured by IncFluid Energy Aljet Inc. (Boise, Id. Telford, Pa.).

Optionally, the method further comprises adjusting the pH of the pharmaceutical formulations by commonly used methods. In one variation, pH is adjusted by addition of acid, such as ascorbic acid, or base, such as sodium hydroxide. In another variation, pH is adjusted and stabilized by addition of buffered solutions, such as solution of (Ethylenedinitrilo) tetraacetic acid disodium salt (EDTA). As decitabine is known to be pH-sensitive, adjusting the pH of the pharmaceutical formulations to approximately pH 7 may increase the stability of therapeutic component.

Optionally, the method further comprises separation of non-dissolved decitabine from the pharmaceutical formulations. Separation may be performed by any suitable technique. For example, a suitable separation method may include one or more of filtration, sedimentation, and centrifugation of the pharmaceutical formulations. Clogging that may be caused by non-dissolved particles of decitabine, may become an obstacle for administration of the pharmaceutical formulations and a potential hazard for the patient. The separation of non-dissolved decitabine from the pharmaceutical formulations may facilitate administration and enhance safety of the therapeutic product.

Optionally, the method further comprises sterilization of the pharmaceutical formulations. Sterilization may be performed by any suitable technique. For example, a suitable sterilization method may include one or more of sterile filtration, chemical, irradiation, heat, and addition of a chemical disinfectant to the pharmaceutical formulation.

As noted, decitabine is unstable in water and hence it may be desirable to reduce the water content of the glycerin. Accordingly, prior to the dissolution and/or sterilization step, the glycerin may be dried. Such drying of glycerin or the solution of decitabine in glycerin may be achieved by the addition of a pharmaceutically acceptable drying agent to the glycerin. The glycerin or decitabine—glycerin formulations may be dried, for example by filtering it through a layer comprising a drying agent.

Optionally, the method may further comprise adding one or more members of the group selected from drying agents, buffering agents, antioxidants, stabilizers, antimicrobials, and pharmaceutically inactive agents. In one variation, antioxidants such as ascorbic acid, ascorbate salts and mixtures thereof may be added. In another variation stabilizers like glycols may be added.

Optionally, the method may further comprise using the pharmaceutical formulations in conjunction with therapeutic components including but not limiting to anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies. The particular examples of therapeutic components are listed in the section 'Decitabine-Glycerin Formulations".

The method described herein provides flexibility wherein stability and therapeutic effect of the pharmaceutical formulations may be further enhanced or complemented.

3. Vessel or Kit Containing Decitabine

The pharmaceutical formulations, described in this invention, may be contained in a sterilized vessel such as syringes, vials or ampoules of various sizes and capacities. The sterilized vessel may optionally contain between 1–50 ml, 1–25 ml or 1–20 ml or 1–10 ml of the formulations. Sterilized vessels maintain sterility of the pharmaceutical formulations, facilitate transportation and storage, and allow administration of the pharmaceutical formulations without prior sterilization step.

The present invention also provides a kit for administering decitabine to a host in need thereof. In one embodiment, the kit comprises decitabine in a solid, preferably powder form, and a non-aqueous diluent that comprises glyercin, propylene glycol, polyethylene glycol, or combinations thereof. Mixing of the solid decitabine and the diluent preferably results in the formation of a pharmaceutical formulation according to the present invention. For example, the kit may comprise a first vessel comprising decitabine in a solid form; and a vessel container comprising a diluent that comprises glyercin; wherein adding the diluent to the solid decitabine results in the formation of a pharmaceutical formulation for administering decitabine. Mixing the solid decitabine and diluent may optionally form a pharmaceutical formulation that comprises between 0.1 and 200 mg decitabine per ml of the diluent, optionally between 0.1 and 100, between 2 mg and 50 mg, 5 mg and 30 mg, between 10 mg and 25 mg per ml of the solvent.

According to the embodiment, the diluent is a combination of propylene glycol and glycerin, wherein the concentration of propylene glycol in the solvent is between 0.1–99.9%, optionally between 1–90%, between 10–60%, or between 20–40%.

Also according to the embodiment, the diluent is a combination of polyethylene glycol and glycerin, wherein the concentration of polyethylene glycol in the solvent is between 0.1–99.9%, optionally between 1–90%, between 10–60%, or between 20–40%.

Also according to the embodiment, the diluent is a combination of propylene glycol, polyethylene glycol and glycerin, wherein the concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–60%, or between 20–40%.

The diluent also optionally comprises 40%, 20%, 10%, 5%, 2% or less water. In one variation, the diluent is anhydrous and may optionally further comprise a drying agent. The diluent may also optionally comprise one or more drying agents, glycols, antioxidants and/or antimicrobials.

The kit may optionally further include instructions. The instructions may describe how the solid decitabine and the diluent should be mixed to form a pharmaceutical formulation. The instructions may also describe how to administer the resulting pharmaceutical formulation to a patient. It is noted that the instructions may optionally describe the administration methods according to the present invention.

The diluent and decitabine may be contained in separate vessels. The vessels may come in different sizes. For example, the vessel may comprise between 1 and 50, 1 and 25, 1 and 20, or 1 and 10 ml of the diluent.

The pharmaceutical formulations provided in vessels or kits may be in a form that is suitable for direct administration or may be in a concentrated form that requires dilution relative to what is administered to the patient. For example, pharmaceutical formulations, described in this invention, may be in a form that is suitable for direct administration via infusion.

4. Methods for Administrating the Pharmaceutical Formultions

The formulations of this invention may be delivered via various routes of administration. They may be administered or co-administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally.

The compounds and/or compositions according to the invention may also be administered or co-administered in slow release dosage forms.

The pharmaceuticals of this invention may be administered by a variety of routes, and may be administered or co-administered in any conventional dosage form. Co-administration in the context of this invention is defined to mean the administration of more than one therapeutic agent in the course of a coordinated treatment to achieve an improved clinical outcome. Such co-administration may also be coextensive, that is, occurring during overlapping periods of time.

The pharmaceutical formulations may be co-administered in any conventional form with one or more member selected from the group comprising infusion fluids, therapeutic compounds, nutritious fluids, anti-microbial fluids, buffering and stabilizing agents. Optionally, therapeutic components including, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies, may be that may be co-administered with decitabine—glycerin formulations. The particular examples of therapeutic components are listed in the section called 'Decitabine—Glycerin Formulations'.

Pharmaceutical formulations according to the present invention provide the further advantage of being directly administrable, (e.g., without further dilution) and thus can be stored in a stable form until administration. Further, because glycerin can be readily mixed with water, the formulations can be easily and readily further diluted just prior to administration. For example, the pharmaceutical formulations can be diluted with water 180, 60, 40, 30, 20, 10, 5, 2, 1 minute or less before administration to a patient.

1) Intravenous Administration

Patients may receive the pharmaceutical formulations intravenously. The preferred route of administration is by intravenous infusion. Optionally, the pharmaceutical formulations of the current invention may be infused directly, without prior reconstitution.

In one embodiment, a decitabine—glycerin formulation is infused through a connector, such as a Y site connector, that has three arms, each connected to a tube. As an example, Baxter® Y-connectors of various sizes can be used. A vessel containing decitabine—glycerin formulation is attached to a tube further attached to one arm of the connector. Infusion fluids, such as 0.9% sodium chloride, or 5% dextrose, or 5% glucose, or Lactated Ringer's, are infused through a tube attached to the other arm of the Y-site connector. The infusion fluids and decitabine—glycerin formulations are mixed inside the Y site connector. The resulting mixture is infused into the patient through a tube connected to the third arm of the Y site connector. The advantage of this administration approach over the prior art is that decitabine is mixed with infusion fluids before it enters the patient's body, thus reducing the time when decomposition of therapeutic formulations may occur due to contact with water. For example, the decitabine is mixed less than 10, 5, 2 or 1 minutes before entering the patient's body.

Patients may be infused with decitabine—glycerin formulations for 1, 2, 3, 4, 5 or more hours, as a result of the enhanced stability of the formulations. Prolonged periods of infusion enable flexible schedules of administration of therapeutic formulations.

Alternatively or in addition, speed and volume of the infusion can be regulated according to the patient's needs. The regulation of the infusion of decitabine—glycerin formulations can be performed according to existing protocols.

The pharmaceutical formulations may be co-infused in any conventional form with one or more member selected from the group comprising infusion fluids, therapeutic compounds, nutritious fluids, anti-microbial fluids, buffering and stabilizing agents. Optionally, therapeutic components including, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies, may be that may be co-infused with decitabine—glycerin formulations. The particular examples of therapeutic components are listed in the section called 'Decitabine—Glycerin Formulations'.

Co-infusion in the context of this invention is defined to mean the infusion of more than one therapeutic agents in a course of coordinated treatment to achieve an improved clinical outcome. Such co-infusion may be simultaneous, overlapping, or sequential. In one particular example, co-infusion of the pharmaceutical formulations and infusion fluids may be performed through Y-type connector.

The pharmokinetics and metabolism of intravenously administered the pharmaceutical formulations resemble the pharmokinetics and metabolism of intravenously administered decitabine. In humans, decitabine displayed a distribution phase with a half-life of 7 minutes and a terminal half-life on the order of 10–35 minutes as measured by bioassay. The volume of distribution is about 4.6 L/kg. The short plasma half-life is due to rapid inactivation of decitabine by deamination by liver cytidine deaminase. Clearance in humans is high, on the order of 126 mL/min/kg. The mean area under the plasma curve in a total of 5 patients was 408 µg/h/L with a peak plasma concentration of 2.01 µM. In patients decitabine concentrations were about 0.4 µg/ml (2 µM) when administered at 100 mg/m$^2$ as a 3-hour infusion. During a longer infusion time (up to 40 hours) plasma concentration was about 0.1 to 0.4 µg/mL. With infusion times of 40–60 hours, at an infusion rate of 1 mg/kg/h, plasma concentrations of 0.43–0.76 µg/mL were achieved. The steady-state plasma concentration at an infusion rate of 1 mg/kg/h is estimated to be 0.2–0.5 µg/mL. The half-life after discontinuing the infusion is 12–20 min. The steady-state plasma concentration of decitabine was estimated to be 0.31–0.39 µg/mL during a 6-hour infusion of 100 mg/m$^2$. The range of concentrations during a 600-mg/m$^2$ infusion was 0.41–16 µg/mL. Penetration of decitabine into the cerebrospinal fluid in man reaches 14–21% of the plasma concentration at the end of a 36-hour intravenous infusion. Urinary excretion of unchanged decitabine is low, ranging from less than 0.01% to 0.9% of the total dose, and there is no relationship between excretion and dose or plasma drug levels. High clearance values and a total urinary excretion of less than 1% of the administered dose suggest that decitabine is eliminated rapidly and largely by metabolic processes.

2) Local Delivery

Optionally, the pharmaceutical formulations of the present invention may be administered or co-administered with a non-decitabine agent via local delivery. Local delivery of the pharmaceutical formulations of this invention can be by a variety of techniques and structures that administer the pharmaceutical formulation at or near a desired site. Examples of local delivery techniques and structures are not intended to be limiting but rather as illustrative of the techniques and structures available. Examples include local delivery catheters, site-specific carriers, implants, direct injection, or direct applications.

Local delivery by a catheter allows the administration of a sequential combination of therapeutic agents and/or compositions directly to the desired site according to the methods of the invention. Examples of local delivery using a balloon catheter are described in EP 383 492 A2 and U.S. Pat. No. 4,636,195 to Wolinsky. Additional examples of local, catheter-based techniques and structures are disclosed in U.S. Pat. No. 5,049,132 to Shaffer et al. and U.S. Pat. No. 5,286,254 to Shapland et al. Generally, the catheter is placed such that the therapeutic agents can be delivered at or near the desired site. Dosages delivered through the catheter can vary, according to determinations made by one of skill, but often are in amounts effective to create a cytotoxic or cytostatic effect at the desired site. Preferably, these total amounts are less than the total amounts for systemic administration of the pharmaceutical s of this invention, and are less than the maximum tolerated dose. Delivery of the pharmaceutical formulations of this invention through catheters preferably should be formulated to a viscosity that enables delivery through a small treatment catheter, and may be formulated with pharmaceutically acceptable additional ingredients (active and inactive).

Local delivery by an implant describes the placement of a matrix that contains the pharmaceutical formulations of this invention into the desired site. The implant may be deposited by surgery or other means. The implanted matrix releases the inventive combination of therapeutic agents and/or compositions by diffusion, chemical reaction, solvent activators, or other equivalent mechanisms. Examples are set forth in Langer (1990) *Science* 249:1527–1533. Often the implants may be in a form that releases the inventive combination of therapeutic agents and/or compositions over time; these implants are termed time-release implants. The material of construction for the implants will vary according to the nature of the implant and the specific use to which it will be put. For example, bio-stable implants may have a rigid or semi-rigid support structure, with inventive combination of therapeutic agents and/or composition delivery taking place through a coating or a porous support structure. Other implants may be made of a liquid that stiffens after being implanted or may be made of a gel. The amounts of inventive combination of therapeutic agents and/or composition present in or on the implant may be in an amount effective to treat cell proliferation generally, or a specific proliferation indication, such as the indications discussed herein.

One example of local delivery of the pharmaceutical formulation of the invention by an implant is use of a bio-stable or bio-absorbable plug or patch or similar geometry that can deliver the inventive combination of therapeutic agents and/or composition once placed in or near the desired site (see for example U.S. Pat. No. 5,429,634 to Narciso).

5. Indications that may be Treated with Pharmaceutical Formulations

The pharmaceutical formulations according to the present invention may be used to treat a wide variety of diseases that are sensitive to the treatment with decitabine.

Preferable indications that may be treated using the pharmaceutical formulations of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), muscular degeneration corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment, the pharmaceutical formulations of the present invention may be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment, the pharmaceutical formulations of the present invention may be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the pharmaceutical formulations of the present invention alone or in conjunction with other anti-RA agents may prevent the formation of new blood vessels necessary to maintain the chronic inflammation and provide the RA patient relief from the symptoms.

In yet another embodiment, the pharmaceutical formulations of the present invention may be used for treating diseases associated with abnormal hemoglobin synthesis. The method comprises administering the pharmaceutical formulations of the present invention to a patient suffering from disease associated with abnormal hemoglobin synthesis. Decitabine containing formulations stimulate fetal hemoglobin synthesis because the mechanism of incorporation into DNA is associated with DNA hypomethylatton. Examples of diseases associated with abnormal hemoglobin synthesis include, but are not limited to, sickle cell anemia and β-thalassemia.

In yet another embodiment, the pharmaceutical formulations of the present invention may be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

Gene activation facilitated by the pharmaceutical formulations of the present invention may induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Although exemplary embodiments of the present invention have been described and depicted, it will be apparent to the artisan of ordinary skill that a number of changes, modifications, or alterations to the invention as described herein may be made, none of which depart from the spirit of the present invention. All such changes, modifications, and alterations should therefore be seen as within the scope of the present invention.

EXAMPLE

Various embodiments of the pharmaceutical formulations according to the present invention were prepared and studied for their stability when stored at 40° C. Table 1 lists percentages of decitabine remaining in active form and percentages of decitabine-related substances in the samples after incubation at 40° C. for 1 week and 2 weeks, respectively. As shown in Table 1, at least 86% of decitabine stays intact in the formulations of the present invention after incubation at 40° C. for 1 week, and at least 77% of decitabine remains in active form after incubation at 40° C. for 2 weeks.

In contrast, it is known that in aqueous solutions currently available in the clinic, decitabine degrades rapidly. For example, the concentration of decitabine decreases by about 10% after 4 hours at 25° C. or by about 10% after 24 hours at 4° C. Thus, less than 50% of decitabine remains in active form after storage at 25° C. for 1 day or at 4° C. for 6 days.

As shown in Table 1, chemical stability of the pharmaceutical formulations according to the present invention is significantly higher than that of decitabine formulated using conventionally methods. Also shown in Table 1, addition of an acidifying agent such as ascorbic acid enhanced the stability of the formulation. Surprisingly, addition of propylene glycol dramatically increased the stability of the formulation: about 98% of decitabine remaining in active form after incubation at 40° C. for 1 week, and 96% after incubation at 40° C. for 2 weeks.

TABLE 1

| Storage at 40° C. | Percent (%) of decitabine remaining in active form | | |
|---|---|---|---|
| | DGF | DGAF (ascorbic acid added) | DGAPG (ascorbic acid and PG added) |
| 7 days | 85.8 | 89.3 | 98.5 |
| 14 days | 76.9 | 79.8 | 95.9 |

1. Decitabine—Glycerin Formulation (DGF)

This example describes the formation of the DGF formulation used in the stability study described in Table 1. The DGF formulation comprises: 20 mg of decitabine and 980 mg of glycerin. The glycerin comprises 3.3% of water. Specific gravity of the glycerin is 1.25. The specific gravity of the formulation is approximately 1.25. The final concentration of decitabine within the formulation is approximately 25 mg/ml.

The formulation was prepared by dissolving micronized decitabine in glycerin. Micronization of decitabine is performed using an air jet mill manufactured by Fluid Energy Aljet Inc. (Telford, Pa.). Decitabine may optionally be micronized until the size of at least 90% of the particles is below 20 microns and the size of at least 50% of the particles is below 10 microns. Solubilization of decitabine within the formulation is facilitated by mechanical agitation performed according to manufacturer's protocols by Silverson homogenizer manufactured by Silverson Machines Inc., (East Longmeadow, Mass.). Mechanical agitation is performed until clear solution is obtained. Further, the formulation is sterilized by filtration through a sterile filter with openings smaller than 0.45 μm. The sterilized formulation is aliquoted as 4 ml portions and kept in sterile glass vials in a dark place at room temperature.

2. Decitabine—Glycerin—Ascorbic Acid Formulation (DGAF)

This example describes the formation of the DGAF formulation used in the stability study described in Table 1. The DGAF formulation comprises: 20 mg of decitabine and 980 mg of glycerin. The glycerin comprises 3.3% of water. Specific gravity of the glycerin is 1.25. The specific gravity of the formulation is approximately 1.25. The final concentration of decitabine within the formulation is approximately 25 mg/ml. The DGAF formulation further comprises 0.05 mg of ascorbic acid.

The formulation was prepared by dissolving crystalline powder of ascorbic acid in glycerin, mixing thoroughly, and dissolving micronized decitabine. Micronization, mechanical agitation, sterilization, and further handling of the formulation was performed as described above.

3. Decitabine—Glycerin—Ascorbic Acid—PG Formulation (DGAPGF)

This example describes the formation of the DGAPGF formulation used in the stability study described in Table 1. The formulation comprises 20 mg of decitabine, 0.05 mg of ascorbic acid; 290 mg of glycerin, and 670 mg of propylene glycol. The glycerin comprises 3.3% of water. Specific gravity of the solvent is approximately 1.09. The specific gravity of the formulation is approximately 1.09. The final concentration of decitabine within the formulation is approximately 22 mg/ml. This formulation is prepared by dissolving crystalline powder of ascorbic acid in propylene glycol, adding glycerin, mixing thoroughly, and dissolving micronized decitabine. Micronization, mechanical agitation, sterilization, and further handling of the formulation is performed as described above.

4. Administration of a Decitabine—Glycerin Formulation

This example describes a method for administering a decitabine—glycerin formulation intravenously. According to this example, the content of a glass vial comprising the formulation is infused directly, without prior reconstitution. The vessel containing the formulation is attached to a tube which is further attached to an arm of a Baxter® Y-connector. Infusion fluid containing 0.9% Sodium Chloride is infused through the tube attached to the other arm of the Y-site connector. Aliquots of the formulation enter the Y-site connector where they are mixed with the infusion fluid. The resulting mixture is infused to the patient through the tube connected to the third arm of the Y-site connector.

Because the pharmaceutical formulation is not diluted with water until just prior to administration, decitabine decomposes less rapidly. As a result, infusion can be performed over a longer period of time. For example, patients may receive the pharmaceutical formulations by this infusion method for over 3 hours, every 8 hours on days 1–3. Treatment may be repeated approximately every 6 weeks for at least 2 courses in the absence of disease progression or unacceptable toxicity. Patients may receive a total of 6 courses of therapy. Patients achieving stable disease, hematological improvement, or partial response may receive a total of 6 courses of therapy. Patients achieving a partial or complete response after 6 courses of therapy may receive additional 4 courses. Patients are followed at 8–10 weeks and then every 3 month thereafter.

While the present invention is disclosed with reference to preferred embodiments detailed above, it is to be understood that these embodiments are intended in an illustrative or exemplary rather than in a limiting sense, as it is contemplated that modifications will readily occur to those skilled in the art, modifications which will be within the spirit of the invention and the scope of the appended claims. All patents, papers, articles, references and books cited herein are incorporated by reference in their entirety.

What is claimed is:

1. A method for administering decitabine to a patient suffering from a disease, comprising:
    providing a first vessel which contains decitabine in solid form and a second vessel which contains a diluent comprising glycerin, propylene glycol, polyethylene glycol or combinations thereof, and less than 40% water in volume in the diluent;
    mixing decitabine from the first vessel with the diluent from the second vessel to produce a liquid pharmaceutical composition; and
    administering to the patient the pharmaceutical formulation.

2. The method of claim 1, wherein the pharmaceutical formulation is administered orally, parenterally, topically, intraperitoneally, intravenously, intraarterially, transdermally, sublingually, intramuscularly, rectally, transbuccally, intranasally, liposomally, via inhalation, vaginally, intraocularly, via local delivery, subcutaneously, intraadiposally, intraarticularly, or intrathecally.

3. The method of claim 1, wherein the pharmaceutical formulation is administrated intravenously.

4. The method of claim 1, further comprising:
    administering to the patient a non-decitabine therapeutic agent in combination with the pharmaceutical formulation.

5. The method of claim 4, wherein the non-decitabine therapeutic agent is selected from the group consisting of antibiotic agents, alkylating agents, retinoids, hormonal agents, plant-derived agents, biologic agents, interleukins, interferons, cytokines, immuno-modulating agents, and monoclonal antibodies.

6. The method of claim 1, wherein the disease is selected from the group consisting of hematological disorders, benign tumor and cancer.

7. The method of claim 1, wherein the step of administering includes:
    diluting the pharmaceutical formulation with an aqueous solution; and
    administering the resulting diluted pharmaceutical formulation;

wherein the dilution is performed 10 hr, 2 hr, 1 hr, 30 min, 10 min, 5 min or less before administration.

8. The method of claim 1, wherein the step of administering includes:
   admixing aliquots of the pharmaceutical formulation with an aqueous solution; and
   infusing the resulting solution into the patient's body.

9. The method of claim 8, wherein a Y connector is used to admix the aliquots of the pharmaceutical formulation.

10. The method of claim 8, wherein infusion is performed over a period at least 3 hours.

11. The method of claim 8, wherein infusion is performed over a period at least 5 hours.

* * * * *